United States Patent [19]

Masai

[11] Patent Number: 5,224,172
[45] Date of Patent: Jun. 29, 1993

[54] COBWEBBING DETECTION DEVICE

[75] Inventor: Tetsuji Masai, Kusatsu, Japan

[73] Assignee: Murata Kikai Kabushiki Kaisha, Kyoto, Japan

[21] Appl. No.: 732,103

[22] Filed: Jul. 18, 1991

[30] Foreign Application Priority Data

Jul. 25, 1990 [JP] Japan .................. 2-78203[U]

[51] Int. Cl.⁵ .............................................. G06K 9/00
[52] U.S. Cl. ....................................... 382/1; 356/238;
356/430; 358/106; 382/8; 382/22
[58] Field of Search ................... 382/1, 8, 30, 22;
356/238, 430, 429; 358/101, 106, 107

[56] References Cited

U.S. PATENT DOCUMENTS

| | | | |
|---|---|---|---|
| 4,590,609 | 5/1986 | Choualet et al. | 382/60 |
| 4,792,981 | 12/1988 | Cahill, III et al. | 382/60 |
| 4,942,618 | 7/1990 | Sumi et al. | 382/8 |
| 4,956,869 | 9/1990 | Miyatake et al. | 382/60 |
| 5,077,806 | 12/1991 | Peters et al. | 382/1 |

FOREIGN PATENT DOCUMENTS 62170726 5/1989 Japan.

Primary Examiner—Joseph Mancuso
Attorney, Agent, or Firm—Spensley Horn Jubas & Lubitz

[57] ABSTRACT

In a cobwebbing detection device of the type in which light illuminates the end surface of a package and a cobwebbed yarn is detected by photographing the end surface by a CCD camera, a cobwebbing detection device has a binary encoder which converts each pixel of the image data into a binary coded data, a storage device, for storing the binary-coded pixel data, and a detection circuit which detects each pixel [1] or [0] in each scanning.

4 Claims, 3 Drawing Sheets

COBWEBBING DETECTION DEVICE

FIELD OF THE INVENTION

The prevent invention relates to a device for examining a package wound by an automatic winding machine, and more particularly, to a cobwebbing detection device for detecting the cobwebbing over the end surface of a package.

RELATED ART STATEMENT

In an automatic winder, a yarn unwound form a fine spinning bobbin is wound around a package which rotates on a drum to form a full package. In such a winding operation, the yarn unwound from the fine spinning bobbin is traversed to wind on a package, but when the running yarn falls to the end surface of the package and then is unwound in the succeeding state, a yarn breakage is caused so that the inspection of the cobwebbing is required. The same applicant has proposed to automatically make various inspections of the packages by the package inspection device (disclosed in Japanese Utility Model Application No. 62-170726). FIG. 6 illustrates the above-mentioned package inspection and processing device. In the same figure, reference number 1 represents a conveyer line for conveying a package P disposed up right on a tray 2 and an inspection box 3 disposed at a suitable position of the conveyor line 1. The inspection box 3 has an inlet-outlet opening 4 with a door 5, for the package P.

Various inspection means 6 are disposed within the inspection box. The invention means 6 comprises a mixed-fiber inspection camera 6a for emitting the ultraviolet rays over the surface of the package P, thereby inspecting the mixed fibers, a cobwebbing detecting camera 6b for detecting the cobwebbing by using the visible light rays, and a bunch-winding inspecting camera 6c for inspecting whether or not a bunch winding is formed in response to the light reflected form the bunch winding portion 8 which is illuminated by the light rays emitted form a light source (not shown). Furthermore, disposed within the inspection box 3 are guide rollers 9, 9 which are disposed over the conveyor line 1 and contact the outer peripheral side surface of the tray 2, and a driving roller 10. As the package P is rotated, the entire surface may be checked for defects. An ejecting line 11 is disposed perpendicular to the conveyor line 1 on the side of the outlet opening of the inspection box 3. Between the conveyor line 1 and the ejecting line 11 is disposed an ejecting means 13 comprising a rotary lever 12 used to transfer a defective package P to the ejecting lien 11 from the conveyor line 1.

With the package inspection and processing device with the construction described above, the winding package P is transported into the inspection box 3 in which various inspections are made by the various inspection means 6. The packages are classified as accepted or defective. An accepted package P is continuously transported by the conveyor line 1 and then packaged, while a defective package P is transferred over the ejecting line 11 by the ejecting means 13.

The cobwebbing detection camera 6b comprises solid picture elements (a CCD camera) and the pixel data obtained by this camera is converted into binary coded data. Cobwebbing is detected where a cobwebbed portion of the yarn is continuously extended slantwise. However, in image of cobwebbed yarn is in the form of an arc because the package P is rotating. Accordingly there arises the problem that the cobwebbing cannot be surely detected by the above-mentioned inspection. More specifically, as shown in FIG. 5a, the cobwebbing occurs at the end surface 14 of the package P when, for example, the package P has a circumference indicated by two-dot-dash line Pd. In the case of detecting the yarn 15 when the package P is rotating and an image producing range 16 of the camera 6b is set at the position surrounded by a dotted line, the cobwebbed yarn 15 is displayed in the form of an arc line 18 on the image 17 produced by the camera 6b. As a result, there exists the problem that the cobwebbing inspection cannot be satisfactorily carried out when cobwebbed yarn is in the form of an arc.

OBJECT AND SUMMARY OF THE INVENTION

The present invention was made to solve the above described problem and it is an object of the present invention to provide a cobwebbing detection device which can detect the cobwebbing in a more reliable manner.

In order to attain the above-described objects, in a cobwebbing detection device of the type in which light illuminates the end surface of a package which is rotating and a cobwebbed yarn is detected by photographing the end surface with a CCD camera, one embodiment of the cobwebbing detection device of the present invention includes a binary encoder which in each scanning by the CCD camera, converts each pixel of the image data into a binary coded data; a storage device for storing the binary-coded pixel data; and a detection circuit which detects each pixel [1] or [0] in each scanning by the image data converted into binary code. In one scanning (y) of an array of pixels in the direction x, the detection circuit detects the point at which [0] changes [1] and selects the point as a starting point F(x, y), whereby whether or not a few pixels [1] exist is detected and which, when [0] is detected, selects this point $(x_1)$ as a reference point to determine the starting point $F(x_1-1, y+1)$ for the next scanning in the direction x, whereby whether a few pixels [1] exist or not is detected, and sequentially changes the starting points in the case of the succeeding scannings, thereby detecting an arc shaped cobwebbed yarn.

With the device with the above-mentioned construction;, in the case of detecting a cobwebbed yarn from a binary-coded pixel data, whether or not a few pixels [1] and [0] exist in the direction x in which the pixels are arrayed is detected by one scanning (y) and in response to the detection result, the next point from which the next scanning (y+1) is started is determined to detect whether or not a few pixels [1] and [0] exist. The above-described step is repeated, whereby the cobwebbing can be correctly detected.

DETAILED DESCRIPTION OF PREFERRED EMBODIMENT

Now the present invention will become more apparent form the preferred embodiment thereof taken in conjunction with the accompanying drawings.

Figure 1:
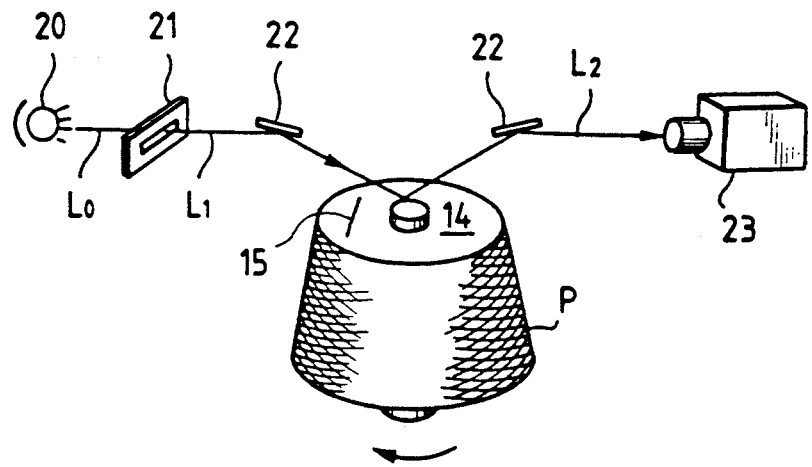
FIG. 1 is a schematic perspective view illustrating a preferred embodiment of the present invention.
Figure 6:
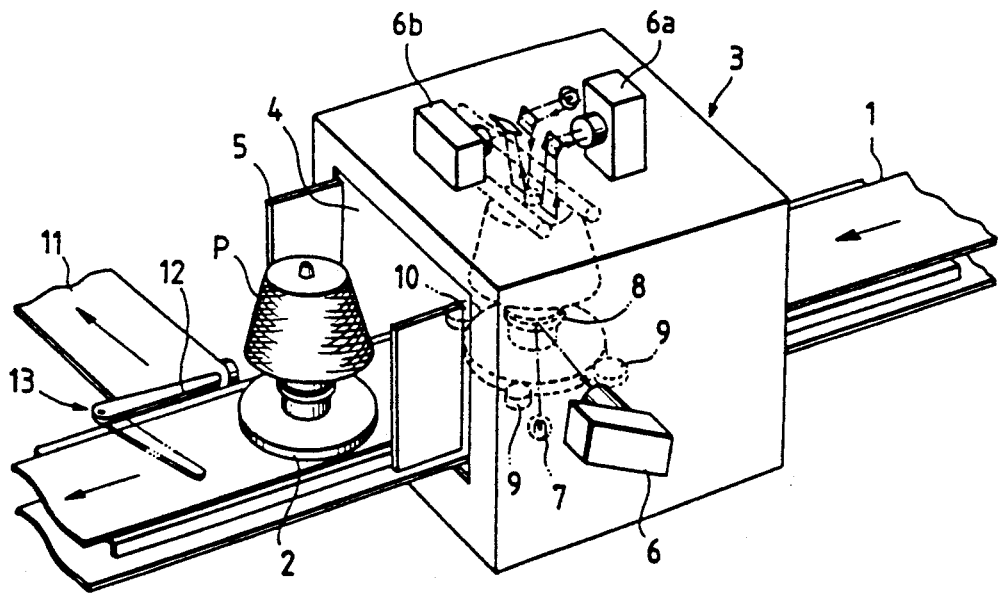
FIG. 6 is a perspective view of a cobwebbing detection device disclosed in the prior application.

A preferred embodiment of cobwebbing detection device in accordance with the present invention is schematically illustrated in FIG. 1, in which reference numeral 20 represents a light source; 21, a slit; 22, mirrors; and 23, a CCD camera. A package P is rotated by the driving roller (not shown) as described above with reference to FIG. 6. The visible light $L_0$ emitted from the light source 20 is converted into a parallel (coherent) light $L_1$ by the slit 21 and then is made to impinge over the end surface 14 of the package P in the radial direction of the end surface substantially as a line. The light $L_2$ reflected from the end surface 14 is reflected by the mirror 22 and transmitted to the CCD camera 23, whereby a picture is taken. When a cobwebbed yarn 15 exists above the end surface 14 of the package P, the shadow of the yarn 15 is formed over the end surface 14 so that the shadow of the yarn 15 is displayed in the image recorded by the CCD camera 23.

Figure 2:
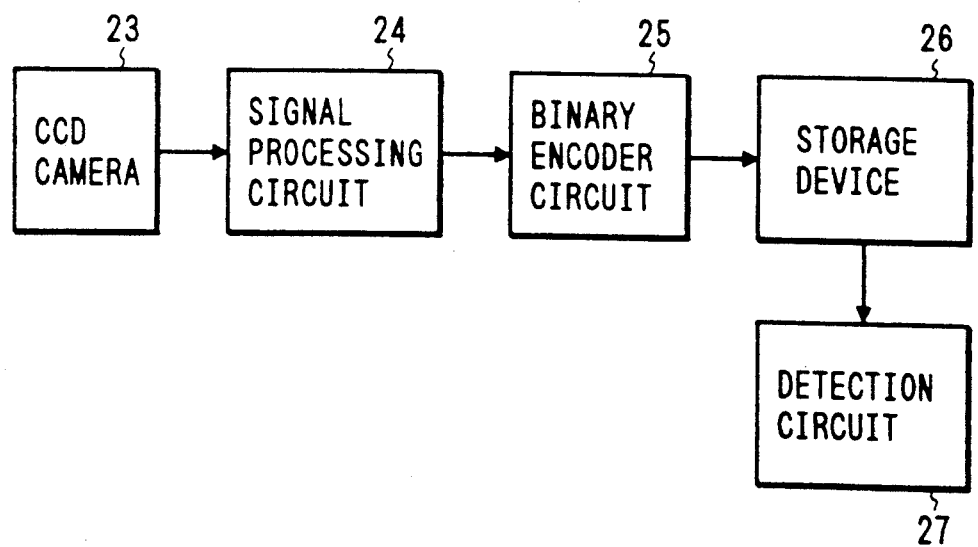
FIG. 2 a block diagram of a detection circuit in accordance with the present invention.

FIG. 2 shows one embodiment of a circuit diagram for processing the image data obtained from the CCD camera 23 and includes a processing circuit 24 for processing the signal delivered from the CCD camera 23, a binary encoder 25 for representing the image data from the processing circuit 24 as each pixel in a binary code, a storage device 26 for storing therein the binary coded data, and a detection circuit 27 for detecting the cobwebbed yarn from the image data stored in the storage device. 26.

In accordance with the preferred embodiment, the signal processing circuit 24 first sequentially processes the image data obtained by each scanning by the CCD camera 23 and the binary encoder 25 converts each pixel received form the signal processing circuit 24 into the binary-coded image data [1] and [0] by each pixel with a certain threshold, which in turn are stored in the storage device 26. The detection circuit 27 detects the cobwebbing in response to the binary coded data received from the storage device 26. FIG. 4a shows the binary-coded image data. In FIG. 4a, the binary coded pixels [1] and [0] of each CCD array are shown in the x direction and the direction y indicates the direction in which the package P is moved (the direction or rotation). Since the end surface 14 of the package P has fine projections and recesses, the image data 30 is dotted with the binary codes [1] and [0] representing black and white pixels, respectively, but the fine projections and recesses on the end surface 14 are distributed at random so that, as shown in FIG. 4b, the detection circuit 27 extracts only the data 31 representing an ordinary cobwebbed yarn whose image is distributed substantially in the form of an arc. The fundamental principle of the detection of the cobwebbing by the detection circuit 27 is as follows. First, whether each pixel is [1] or [0] is detected by each scanning of the binary-coded image data. One scanning (y) is started from a starting point $F(x, y)$ at which [0] is followed by [1] in the array in the direction x, thereby detecting whether or not a few pixels [1] exist. When [0] is detected, the position of the detected [0] is determined as a reference point $(x_1)$ and the starting point $F(x_1-1, y+1)$ in the direction x for the next scanning $(y+1)$ is determined. The above-described step is repeated, thereby an arc-shaped cobwebbed yarn is detected as will be described in more detail with reference to FIG. 3.

Figure 3:
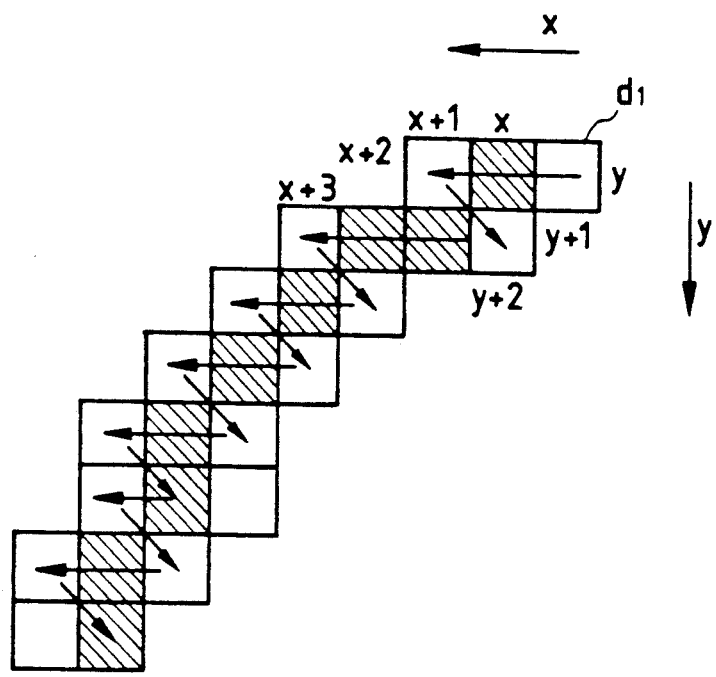
FIG. 3 is a view to explain how a cobwebbed yarn is detected.
Figure 4A:
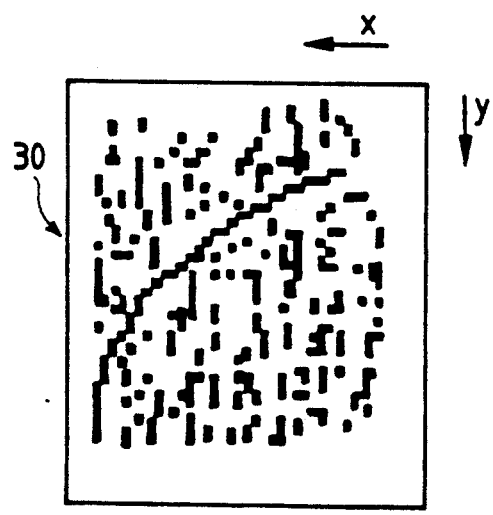
FIG. 4 is a view, on an enlarged view, illustrating a major portion of the binary-coded image data.
Figure 4B:
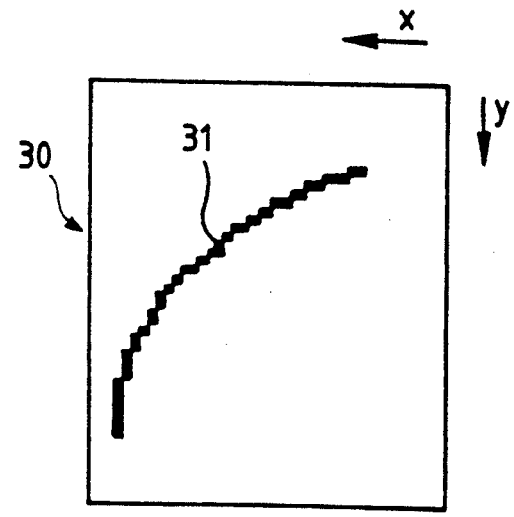
Figure 5A:
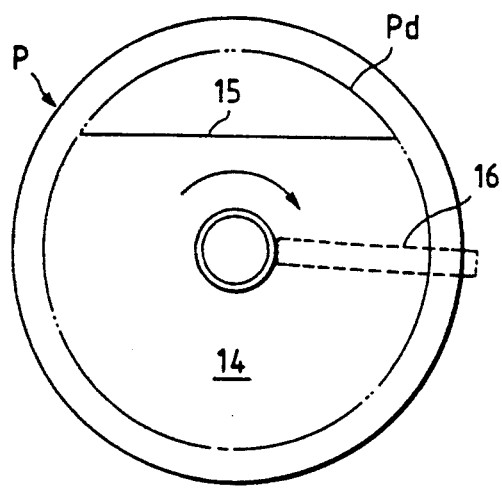
FIG. 5 is a view illustrating the relationship between a cobwebbed yarn of a package and the image thereof detected in a CCD image.
Figure 5B:
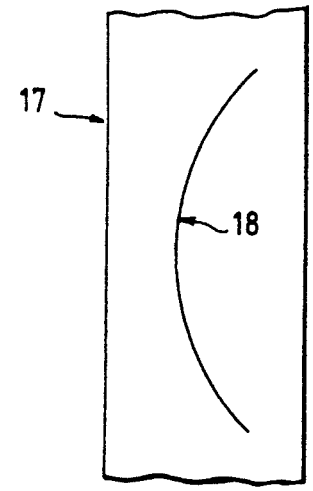

FIG. 3 illustrates the pixel data 32 in the vicinity of the cobwebbed yarn in which each pixel is enlarged in both the x and y directions.; the hatched pixel represents [1] while the white pixel represents [0]. It is now assumed that in the direction x at one scanning position (y), the pixel indicated by dl is [0] and the succeeding pixel is [1] which is followed by the pixel [0]. Then, the pixel [1] is determined as the starting point (x, y). The pixel (x+1) adjacent to the starting point F (x, y) is [0] so that the position of this pixel $(x_1=x+1)$ is selected as a reference position and the starting point $F(x_1-1=x, y+1)$ of the next scanning $(y+1)$ is determined. From this starting point $F(x_1-1=x, y+1)$, the detection whether or not the pixel [1] exists in the direction x is carried out. In the case of he scanning $(y+1)$, [0] is $x+3$ so that the starting point F of the next scanning $(y+3)$ becomes $(x_1-1=x+3, y+2)$. The above step is repeated so as to detect the cobwebbed yarn. According to the above-described detection method, the cobwebbed yarn defines a continuous image so that the yarn can be correctly detected by detecting whether or not [1] exists in unit consisting of a few pixels. Furthermore, the starting point is suitably changed for each scanning, an arc shaped cobwebbed yarn can be correctly detected. The pixels of the fine projections and recesses are discontinuous so that during the detection whether or not [1] exists by changing the scanning starting points, it becomes impossible to detect [1] and the scanning is terminated at the position where no [1] cannot be detected so that the image of the cobwebbed yarn can be easily distinguished from the images of the fie projections and recesses.

It is apparent that the detection whether pixel [1] exists or not in the x direction form the starting point can be suitably changed depending upon the pixel density of each CCD array, the size of an image of a real package focused upon the CCD array and the thickness of a yarn. In short, it suffices that the image of a cobwebbed yarn is sufficiently formed within a range consisting of a few pixels.

As is apparent from the above-description, the present invention can attain the following effects and features. In the case of the detection of cobwebbing from the binary coded pixel data, one scanning (y) detects whether a few pixels [1] and [0] in an array extended in the direction x and in response to the result of the above detection, the starting point of the next scanning $(y+1)$ is determined to detect whether a few pixels [1] and [0] exist. By repeating the above-described step, a cobwebbed yarn can be correctly detected. The automatic detection of cobwebbed yarn can be accomplished in a correct manner.

What is claimed is:

1. A device for detecting an irregular condition on a package, comprising:

light means for illuminating a surface of the package;

camera means for photographing the illuminated surface of the package and for producing image data comprising pixels;

encoder means for converting the pixels of image data into pixels of binary coded data, each pixel of binary coded data defining one of a 1 and a 0;

storage means for storing the pixels of binary coded data in a two dimensional array, the array defining a first direction and a second direction;, the first direction being substantially perpendicular to the second direction;

scanning means for scanning the pixels of binary coded data in the first direction form a first starting pixel until a detection of a pixel defining a 0, for setting a second starting pixel in response to the detection of a pixel defining a 0, the second starting pixel spaced one pixel in the second direction and one pixel in a direction opposite the first direction from the detected pixel defining a 0, and for scanning the pixels in the first direction from the next starting pixel and determining means for determining whether the scanned pixels of binary coded data correspond to an irregular condition on the package.

2. The device of claim 1, wherein the camera means comprises a CCD camera.

3. The device of claim 1, wherein the surface of the package defines a plane and the pixel defining a 1 is indicative of an area on the surface of the package which extends out of the plane.

4. The device of claim 1, wherein the first starting pixel comprises a pixel defining a 1 is located one pixel in the first direction form a pixel defining a 0.

* * * * *